United States Patent
Backhaus-Ricoult

(10) Patent No.: US 9,688,647 B2
(45) Date of Patent: Jun. 27, 2017

(54) ALKYLENE OXIDE SYNTHESIS

(71) Applicant: Corning Incorporated, Corning, NY (US)

(72) Inventor: Monika Backhaus-Ricoult, Bourron (FR)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 15/034,742

(22) PCT Filed: Nov. 4, 2014

(86) PCT No.: PCT/US2014/063772
§ 371 (c)(1),
(2) Date: May 5, 2016

(87) PCT Pub. No.: WO2015/073249
PCT Pub. Date: May 21, 2015

(65) Prior Publication Data
US 2016/0280674 A1    Sep. 29, 2016

Related U.S. Application Data

(60) Provisional application No. 61/904,575, filed on Nov. 15, 2013.

(51) Int. Cl.
*C07D 301/00* (2006.01)
*C07D 301/10* (2006.01)
(Continued)

(52) U.S. Cl.
CPC .......... *C07D 301/10* (2013.01); *B01J 23/002* (2013.01); *B01J 23/34* (2013.01); *B01J 23/83* (2013.01);
(Continued)

(58) Field of Classification Search
CPC .......... C07D 301/10; C25B 3/04; C25B 9/08; C25B 11/0478; C25B 13/04; B01J 23/002; B01J 23/34; B01J 23/83
(Continued)

(56) References Cited

U.S. PATENT DOCUMENTS 3,922,204 A    11/1975   Tseung et al.
4,092,227 A    5/1978    Haidinger
(Continued)

FOREIGN PATENT DOCUMENTS

EP    0480116         4/1992
EP    0712851    *    5/1996
KR    201000115650    10/2010

OTHER PUBLICATIONS

International Search Report and the Written Opinion of the International Searching Authority, Dec. 22, 2014, 5 Pages, EPO.
(Continued)

*Primary Examiner* — T. Victor Oh
(74) *Attorney, Agent, or Firm* — Zachary J. Wegmann

(57) ABSTRACT

Direct epoxidation of propene is carried out on electrochemically tuned mixed oxide catalyst surfaces in a single chamber reactor with mixed reaction gas of hydrocarbon and oxygen. Yield and selectivity improvement compared to platinum- or silver-based noble metal catalysts have been demonstrated for the same reactor set up. Increase in propylene oxide yield has been demonstrated when a cell voltage is applied.

17 Claims, 17 Drawing Sheets

(51) Int. Cl.
| | |
|---|---|
| C07D 301/04 | (2006.01) |
| B01J 23/00 | (2006.01) |
| B01J 23/34 | (2006.01) |
| B01J 23/83 | (2006.01) |
| C25B 3/04 | (2006.01) |
| C25B 9/08 | (2006.01) |
| C25B 11/04 | (2006.01) |
| C25B 13/04 | (2006.01) |
| B01J 35/00 | (2006.01) |
| B01J 37/02 | (2006.01) |

(52) U.S. Cl.
CPC .............. *C07D 301/04* (2013.01); *C25B 3/04* (2013.01); *C25B 9/08* (2013.01); *C25B 11/0478* (2013.01); *C25B 13/04* (2013.01); *B01J 35/0033* (2013.01); *B01J 37/0215* (2013.01)

(58) Field of Classification Search
USPC ........................................................ 549/536
See application file for complete search history.

(56) References Cited

U.S. PATENT DOCUMENTS

| | | |
|---|---|---|
| 4,329,208 A | 5/1982 | Vayenas et al. |
| 4,643,806 A | 2/1987 | Hegedus et al. |
| 5,089,455 A | 2/1992 | Ketcham et al. |
| 5,527,436 A | 6/1996 | Cooker et al. |
| 6,548,682 B1 | 4/2003 | Weisbeck et al. |
| 2005/0059244 A1 | 3/2005 | Lohrberg et al. |
| 2005/0190088 A1 | 9/2005 | Fey et al. |
| 2010/0160654 A1 | 6/2010 | Grey |

OTHER PUBLICATIONS

R.Zenteno, L.Vicente, T.Viveros, Mat. Res. Soc. Symp. Proc. vol. 549, 111 (1999).

P.Beatrice, C.Pliangos, W.Worrel, C.Vayenas, Solid State Ionics 136, 833 (2000).

Otsuka, Kiyoshi: 11 Reductive and Oxidative Activation of Oxygen for Selective Oxygenation of Hydrocarbons 11, Studies in Surface Science and Catalysis ,110(3rd World Congress on Oxidation Catalysis, 1997), 93-102 Coden: SSCTDM;ISSN: 0167-2991,1997, XP009181684, Abstract p. 96; Fig 2 p. 99; Fig 5.

L Holbrook: 11 Electrooxidation of Olefins at a Silver Electrode 11, Journal of Catalysis, vol. 38, No. 1-3, Jun. 1, 1975 (Jun. 1, 1975): pp. 294-298, XP55158229,ISSN: 0021-9517, DOI:10.1016/0021-9517 (75)90090-1 Abstract p. 294, p. 295 p. 297.

E.Mutoro, C.Koutsodontis, B.Luerssen, S.Broda, C.Vayenas, J.Janek, Applied Catalysys B 100, 328 (2010).

Haruta, "Catalysis of Gold Nanoparticles Deposited on Metal Oxides" Jun. 2002, vol. 6, issue 3, pp. 102-115.

Stoukides, M. et al: "Electrochemical modification of the activity and selectivity of silver for light olefin oxidation" 1984, vol. 4, IV827-IV833.

\* cited by examiner

ALKYLENE OXIDE SYNTHESIS

CROSS-REFERENCE TO RELATED APPLICATIONS

This application claims the benefit of priority under 35 U.S.C. §119 of U.S. Provisional Application Ser. No. 61/904,575 filed on Nov. 15, 2013, the content of which is relied upon and incorporated herein by reference in its entirety.

FIELD

The present disclosure relates to synthesis of alkylene oxides such as propylene oxide; more particularly to alkylene oxide synthesis with mixed oxide catalyst.

BACKGROUND

Industrial production of ethylene and propylene oxide (PO) reaches 15 and 3 mill tons/year world-wide, respectively, and is steadily growing. The corresponding market for PO alone can be estimated as about $20 billion per year. Major applications of propylene oxide include production of polyethers, polyols (propylene glycol), polyurethanes and propylene-carbonates. Glycol ethers and polyglycol are used as solvents for paints, coatings, inks, dyes and cleaners. Propylene glycol is used for food flavoring, coloring and fragrance oils, industrial and medical lubricants. Polyether polyols are used for making polyurethane foams.

While ethylene epoxidation is industrially implemented as direct oxidation on silver catalysts and reaches more than 90% yield and very high selectivity, production of PO by direct oxidation is typically far less successful, providing yields in the range of only 1% and very low selectivity. Therefore, propylene oxide needs are currently covered at an industrial scale by two more complex indirect processes, a peroxidation process and a hydrochlorination route. In the past, production was covered primarily by the chlorohydrin process; however, the oxidation process is lately gaining in importance.

While direct epoxidation of ethylene on Ag-based catalysts produces only few side products besides epoxide and full combustion products $CO_2$ and $H_2O$ and therefore can easily be used as an industrial production process, direct oxidation of propylene produces a large variety of side products, such as propanal, acrolein, allyl alcohol, acetone, acid, dimers and higher polymerization products. Most side products form from various intermediate metallocyclic complexes of adsorbed oxygen with olefin on the catalyst surface. Because propylene oxide is the species that most easily transforms back into an oxygen adsorbate or other surface complex, experimental synthesis conditions typically promote low gas concentration, short contact time (high pressure) and very dry conditions.

Research has been carried out to identify suitable direct oxidation processes for production of PO. However, many of these processes continue to suffer from low yield and selectivity or cost barriers for large scale synthesis. For example, at least one disclosed direct oxidation method is carried out under hydrogen, which can drive high production costs. With some processes, poisoning of catalyst results in decreased performance over time, which can occur rapidly. Photon-enhanced direct epoxidation with a Cu-based catalyst has also been used to produce PO.

BRIEF SUMMARY

The present disclosure describes, among other things, the direct epoxidation of propene on electrochemically tuned oxide catalyst surfaces. For example, the results presented herein demonstrate the direct epoxidation of propene on electrochemically tuned mixed oxide catalyst surfaces in a single chamber reactor with mixed reaction gas of hydrocarbon and oxygen. Yield and selectivity improvement compared to platinum- or silver-based noble metal catalysts are demonstrated. Further, propylene oxide yield increases when a cell voltage is applied. The described process allows production of propylene oxide at lower cost due to process simplification. The low cost oxide catalyst also allows savings compared to use of high cost noble metals.

In embodiments described herein, a metal oxide catalyst can be electrochemically tuned to a state with improved catalyst performance, relative to un-tuned catalyst. While not intending to be bound by theory, it is believed that the improved performance of the tuned catalyst results from active oxygen species, charge carriers and active sites at a reaction surface of the catalyst to promote redox-reactions or Lewis acid/base reactions.

The catalyst can comprise a mixed oxide surface containing elements that can adopt different oxidation states. One example of such a mixed oxide catalyst is a mixed perovskite catalyst, such as a Fe- or Mn-perovskite catalyst. Examples of mixed oxide catalysts include, but are not limited to, $(La,Sr)FeO_3$, $(La,Sr)MnO_3$. Additionally strontium can be substituted with any other transition metal, Ba or Ca. In addition or alternatively, another rare earth metal can be substituted for La.

The catalyst can be part of an electrochemical cell to allow electrochemical tuning of the catalyst and its surface. The catalyst can be supported by a solid electrolyte, and the cell can contain a counter electrode. The electrolyte can be an oxygen-ion conducting electrolyte, such as doped zirconia.

The electrochemical cell can be part of a reaction system including a reaction chamber housing the cell. The reactor's electrochemical cell can be run at zero potential, under negative or positive voltage. It has been found that good yield and selectivity are achieved with mixed oxide catalysts, when the catalyst is part of an electrochemical cell with an oxygen-ion conducting electrolyte by applying a cell voltage. Good catalyst performance has been achieved under oxygen excorporation at the catalyst surface (anodic operation).

In embodiments, a method for producing propylene oxide includes reacting oxygen and propene in the presence of a metal oxide catalyst that serves as an electrode of an electrochemical cell to produce propylene oxide. The ratio of propene to oxygen is about 0.5:1 or greater.

In embodiments, a method for producing propylene oxide that includes reacting oxygen and propene in the presence of a metal oxide catalyst free of a noble metal to produce propylene oxide. The ratio of propene to oxygen is about 0.5:1 or greater.

One or more embodiments of the chemical synthesis methods described herein provide one or more advantages over prior methods related to synthesis of alkylene oxides such as propylene oxide. For example, a direct oxidation process to produce propylene oxide as described herein offers process cost savings relative to existing processes due, at least in part, to lower process complexity, eliminated need of additional precursor chemicals and handling of their products after reaction. In addition, cost of oxide catalyst material described for use in various embodiments herein is lower than noble metal catalyst cost. Further, embodiments of the processes described herein provide higher selectivity than currently reported selectivity. Moreover, embodiments of the catalysts described herein can be electrochemically regenerated or regenerated in oxygen to avoid or mitigate the problem of catalyst aging. Accordingly, tuned oxide catalysts as described herein should result in less aging then reported noble metal catalysts, and therefore should provide benefit through larger lifetime. These and other advantages will be readily understood from the following detailed description when read in conjunction with the accompanying drawings.

BRIEF DESCRIPTION OF THE DRAWINGS

FIG. 4A: XRD of electrolyte-supported perovskite catalyst after long-time operation in propene/oxygen at 550° C. reveals only a single perovskite phase in the $(La_{0.8}Sr_{0.2})FeO_3$ catalyst layer. FIG. 4B: SEM of polished cell cross sections of an operated cell with LSF catalyst shows no microstructural modification of the catalyst or the catalyst/electrolyte interfaces. FIG. 4C: Oxygen incorporation rates in propene/oxygen mixtures compared to those in oxygen are similar for LSF and significantly accelerated for LSM, demonstrating that the oxide catalyst surface is not degraded by operation in propene-containing gas mixtures, FIG. 4D: Oxygen incorporation rates in humid air compared to those in dry oxygen are similar for LSF, demonstrating that the catalyst is not destroyed by the potential side product water.

FIG. 7A shows results for gas combustion of 1% $O_2$ and 1.8% propene in argon as function of temperature. It includes the unconverted fraction of propene, propylene oxide yield and the selectivity for propylene oxide. The reactions initiates at around 300° C. The main reaction products are $CO_2$ and $H_2O$. At high temperature, 700° C. and more, almost all oxygen is consumed under $CO_2$ formation (threshold 12%). FIG. 7B presents propylene oxide yield as function of temperature for gas combustion with different gas mixtures of propene and oxygen.

Figure 1:
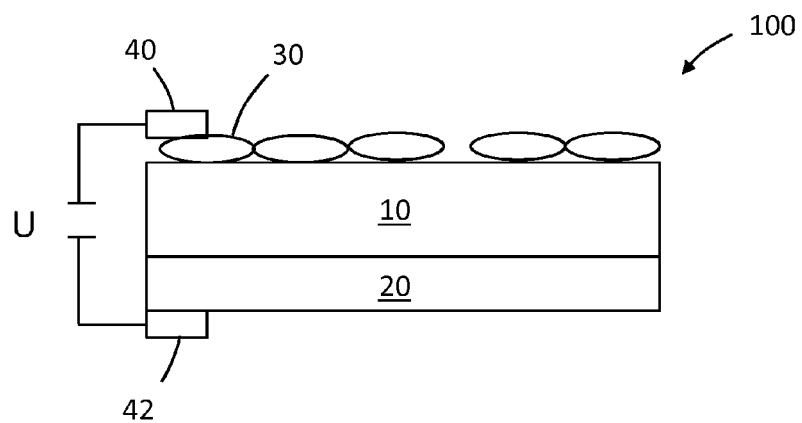
FIG. 1 is a schematic side view and block diagram of an embodiment of an electrochemical cell including catalytic electrode surface.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and can be made without departing from the scope or spirit of the present disclosure. The following detailed description, therefore, is not to be taken in a limiting sense.

The present disclosure describes, among other things, synthesis of propylene oxide by direct epoxidation of propene on metal oxide catalyst surfaces. The catalytic surfaces are, in embodiments, free of noble metals. In the Examples presented herein, yield and selectivity are improved compared to platinum- or silver-based noble metal catalysts. The metal oxide catalytic surfaces can serve as surfaces of electrodes of electrochemical cells such that a voltage can be applied to the cell to electrochemically tune the metal oxide catalyst (e.g., tune the oxidation state of the metal oxide catalyst). Accordingly, the catalyst can comprise a mixed oxide surface containing elements that can adopt different oxidation states and thus are electrochemically tunable. As shown in the Examples presented herein, an increase in propylene oxide yield can be achieved when a voltage is applied to an electrochemical cell comprising the metal oxide as a surface of an electrode.

Any suitable metal oxide can be used for catalyzing the direct epoxidization of propene. In embodiments, the metal oxide comprises a transition metal. In embodiments the metal oxide catalyst comprises a mixed metal oxide. In embodiments the metal oxide catalyst is a perovskite catalyst. Perovskite catalysts are catalysts having the formula $ABO_3$, where 'A' and 'B' are two cations. Typically, the 'A' atoms are larger than the 'B' atoms. Perovskite catalysts can be considered as interesting oxidation/reduction catalysts due to the ability of their transition metals to adopt different oxidation states and the ability of their crystal structure to adopt oxygen deficiency, A or B excess and undergo reversible transformations into brownmillerite and pyrochlore phases, all of which occurs with even wider flexibility at the surface of the perovskites compared to their bulk material and thus enables the materials to act as catalysts by enabling charge carrier or oxygen transfer in oxidation (or reduction) reactions.

In embodiments, the catalyst comprises an Fe- or Mn-perovskite, such as $(La,Sr)FeO_3$ or $(La,Sr)MnO_3$. In embodiments, Fe and Mn can be partially substituted by other transition metals including Fe, Mn, Co, Ni, Cr, etc or a mixture thereof. In embodiments, Ba or Ca or a mixture of any two or all three is substituted for strontium. In embodiments, another rare earth metal or rare earth metal mixture is substituted for La.

Incorporation of the catalyst into an electrochemical cell allows for tuning of the electrochemical state of the catalyst or regeneration of the catalyst. The electrochemical cell can be subjected to no voltage, positive voltage or negative voltage, as appropriate. By subjecting the cell to a voltage, the catalytic surface can be tuned and the catalytic efficiency and effectiveness can be enhanced. Electrochemical tuning can result in injecting charge carriers and oxygen into the catalyst or extracting oxygen from the catalyst by using an electrochemical cell with an oxygen ion electrolyte that supports the oxide catalyst (electrode) and by driving oxygen injection into (extraction from) the catalyst via the cell potential in order to tune the oxide catalyst surface electronic structure and surface oxygen species. Continuous tuning of the catalyst surface is possible via the cell voltage. A positive cell voltage produces excorporation of oxygen at the oxide catalyst surface and typically goes hand in hand with the formation of more oxidized catalyst surface states and special oxygen species at the surface. A negative cell voltage drives oxygen incorporation at the catalyst surface and favors more reduced catalyst surface states.

When no cell voltage is applied or when an oxide catalyst is employed in the absence of an electrochemical cell, intrinsic surface defects such as, for example, oxygen vacancies and transition metal with unique or mixed oxidation states can interact with oxygen and hydrocarbon to catalyze oxidation of the hydrocarbon. When a cell voltage is applied, the catalytic surface defects are modified (e.g., oxygen ion injection into the catalyst or extraction from the catalyst at negative voltage, modified oxidation states and surface states, etc.) and interaction with hydrocarbon and oxygen gas molecules is altered, thereby modifying the catalyst reactivity. Examples of surface modifications that can result from application of a voltage to the cell include modification of electrostatic effects, modification of redox potential, modification of oxygen pumping or extraction, spilling of electric carriers, back-spilling of ionic carriers, surface segregation, and surface diffusion.

While not intending to be bound by theory, it is believed that the surface of an oxide catalyst can be tuned by electrochemically providing oxygen (or proton) and electrons to the catalyst surface and tuning the catalyst surface such that the surface shows improved catalyst performance. The improved performance of the tuned catalyst can result from active oxygen species, charge carriers and active sites at the catalytic surface so that redox-reactions or Lewis acid/base reactions are promoted. The oxide catalyst can possess electric (and ionic) conductivity, and can be supported by an ion conductor and, as electrode, can be part of an electrochemical cell with a counter electrode. The oxide catalyst and especially its surface can be tuned via applied cell voltage.

Referring now to FIG. 1, a schematic drawing of an example of an electrochemical cell 100 incorporating a metal oxide catalyst as an electrode 30; e.g., a catalyst as described above, is shown. The depicted cell 100 includes an electrolyte 10 disposed between the catalyst electrode 30 and a counter electrode 20. The electrolyte 10 can be a solid electrolyte that supports the catalyst electrode 30. In an embodiment, the electrolyte 10 can be an oxygen ion conducting electrolyte through which oxygen ions can be pumped into or out of the catalyst. Examples of solid oxygen ion conducting electrolytes that can be used are doped zirconia containing electrolytes, such as yttria stabilized zirconia films. One example of a yttria stabilized zirconia film is a 3YSZ (3 mol % yttria stabilized zirconia) electrolyte film (e.g., as described in U.S. Pat. No. 5,089,455). Of course, other stabilized zirconia electrolytes can also be used, such as other tetragonal or cubic zirconia containing Mg, Ca, different rare earth elements, manganese, or the like. Other suitable solid oxygen ion conducting electrolytes such as doped ceria (for example $(Ce, Gd)O_{2-x}$, LSGM (for example $La_{0.9}Sr_{0.1}Ga_{0.8}Mg_{0.2}O_{2.85}$), BICUVOX (for example $Bi_2V_{1.9}Cu_{0.1}O_{5.35}$) can also be employed.

Any suitable counter electrode 20 can be used. In embodiments, the counter electrode 20 can be either a symmetric counter piece of the working electrode in case of use of symmetric cells or formed from relatively inert material, such as a noble metal/ceramic composite or pure noble metal, with the ceramic being for example stabilized zirconia and the noble metal being silver, platinum, iridium, platinum/iridium, gold, or the like.

The electrochemical cell 100 depicted in FIG. 1 also includes contact 40 electrically coupled to the catalyst electrode 30 and contact 42 electrically coupled to the counter electrode 20. The contacts are part of a circuit for applying a voltage (U) to the cell. Any suitable material can be used for forming contacts 40, 42. Examples of suitable materials include those discussed above as suitable materials for forming counter electrode 20. In embodiments, contacts 40, 42 are formed from platinum, silver or gold.

An electrochemical cell, e.g. electrochemical cell 100 depicted in FIG. 1, can be formed in any suitable manner. By way of example, an electrolyte film, such as a 3YSZ film or other suitable film, can be used as a substrate onto which either two catalyst electrodes or a counter electrode and a catalyst electrode can be deposited (onto opposing major surfaces). Any suitable deposition process, such as vapor deposition, laser deposition, printing, plating, sol gel, salt, organic or polymer precursor decomposition etc., can be used. In embodiments, the catalyst electrode can be deposited by printing. For example, metal oxide catalyst particle can be mixed with a printed vehicle and printed onto a surface of the electrolyte film and fired at appropriate temperatures for appropriate times. The catalyst electrode can be of any suitable thickness. In embodiments, the catalyst electrode has a thickness of less than about 10 micrometers, such as less than about 5 micrometers, or from about 1 micrometer to about 3 micrometers. In some cases, the catalyst electrode is not printed directly on the electrolyte, but on one or more sublayers that can have functions such as providing adhesion, protecting the catalyst from chemical reaction with the substrate, etc. The different layers can be processed by the before-mentioned techniques one-by-one and can either be co-fired or fired one-by-one after each processing step. Catalyst electrode and counter electrode can also be fired together or in different steps.

Electrically conducting contacts can be applied in any suitable manner, such as printing, etc. In embodiments, an electrically conducting wire can be simply contacted with the catalyst electrode or counter electrode and soldered, welded, etc. to form a stable electrical connection. In embodiments, suitable contact material; e.g. silver, gold or platinum, can be mixed with stabilized zirconia powder and printing vehicle into a paste and applied on top of a catalyst electrode surface. In embodiments, the catalyst material covers the complete electrode surface, while the mixture comprising contact material can be deposited in a patterned manner, such as a comb-shaped pattern or net of different spacing and shape, over the catalyst electrode. In such embodiments, a substantial portion of the catalyst surface can be left uncovered by the patterned deposited material. In embodiments, less than 50% of the catalyst layer can be covered by the contact layer. In embodiments, less than 30% of the catalyst layer can be covered by the contact layer. In embodiments contact layer can be highly porous with large pores so that gas can easily penetrate through that layer and access the catalyst.

The catalysts or electrochemical cells described herein can be used for catalysis of any suitable reaction. In embodiment, the catalysts or electrochemical cells are used to catalyze the synthesis of an alkylene oxide by direct epoxidation of an alkene. The alkene can be a lower alkene, such as a $C_3$-$C_6$ or a $C_3$-$C_4$ alkene. In some embodiments, the alkene can be propene and the alkylene oxide can be propylene oxide. In some embodiments the surface of the catalyst can be tuned to enhance efficiency and selectivity of the epoxized product.

A number of different oxidized species of propene can result. Accordingly, enhancing selectivity and yield of propylene oxide can be important factors in producing a commercially reasonable production process. In embodiments, propylene ($CH_3CHCH_2$) and oxygen (½ $O_2$) are used as starting reagents, which can interact with the catalyst to result in a number of oxidized species, which oxidized species can further interact with the catalyst and oxygen to produce a variety of potential products, including $CO_2$ and $H_2O$ if the propene is fully combusted. Some of the reaction products that can be result include acetone, propylene oxide, propanal, acrolein, and allyl alcohol. Full combustion, allylic H-abstraction, scavenging by adsorbed oxygen, hydroxyl recombination, etc. can be result in $CO_2$ and $H_2O$ end products.

Embodiments of the processes described herein result in direct propylene epoxidation on a mixed oxide catalyst surface with higher yield and higher selectivity than on noble metal catalysts, such as Ag or Pt, under the same experimental conditions. For a perovskite catalyst supported by an oxygen ion electrolyte, such as yttria stabilized zirconia, and part of an electrochemical cell through which oxygen ions can be pumped into or out of the catalyst (which acts as electrode), the epoxide yield can be modified by an applied cell voltage. For $(La,Sr)MnO_3$ catalyst, an increase in propylene oxide yield of up to 50% can be demonstrated in a desirable range of cell voltage from +0.1V to +1V. The yield and selectivity for other mixed oxide catalysts in electrochemical cells using the same or similar oxygen ion conducting electrolytes (or for $(La,Sr)MnO_3$ catalyst in a cell using a different oxygen ion conducting electrolyte) can also be readily enhanced by those of skill in the art by adjusting the cell voltage as appropriate or needed.

Figure 2:
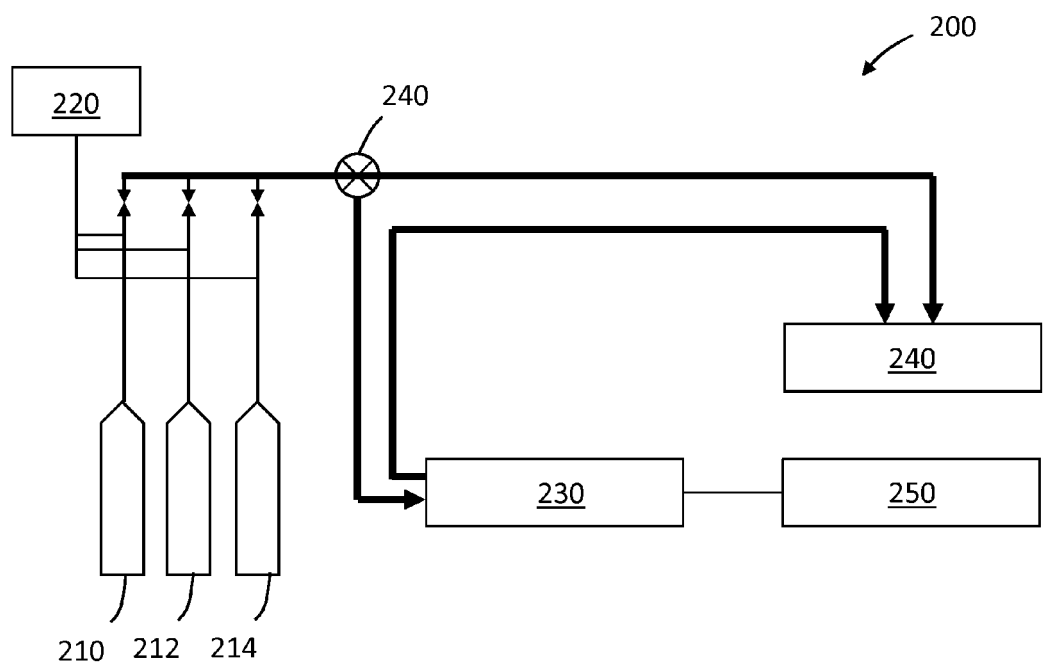
FIG. 2 is a schematic block diagram of the used testing set up, including a reaction chamber.

Referring now to FIG. 2, a schematic drawing is shown of an example of a system 200 used for experimental purposes disclosed herein. The system 200, or components thereof, can be used for larger scale manufacturing of propylene oxide or other alkylene oxides. The system 200 includes gas sources of starting reagent 210, 212, such as propene and oxygen, and a supply 214 of inert gas, such as argon or nitrogen. The depicted system includes a gas mixer and flow controller 220 and valve 230 for controlling flow to reaction chamber 230 or gas analyzer 240, such as an in-line gas chromatograph instrument. Gas from reaction chamber 230 can be also flow to gas analyzer 240 so that starting products from sources 210, 212 can be compared to reaction products from reaction chamber 230 for purposes of evaluating yield, efficiency, selectivity, etc. Within the reaction chamber 230, an electrochemical cell (not shown in FIG. 2), such as a cell 100 depicted in FIG. 1, can be disposed. The electrochemical cell can be operably coupled to an impedance analyzer 250 for purposes of controlling or maintaining voltage across the cell.

As discussed in more detail below in the Examples, performance of electrolyte-supported perovskites as direct epoxidation catalysts for propene is demonstrated in oxygen-propene gas mixtures (diluted in inert gas $N_2$ or Ar) with 0.2-2% propene under applied electric cell potential in a small electrochemical reactor. Propylene epoxide is shown to form with perovskite catalysts. The evolution of yield with temperature, propene/oxygen ratio and gas flow rate suggest an operation window around 450-550° C., in which the contribution of gas combustion with its low selectivity remains negligible. For $(La_{1-x}Sr_x)FeO_3$ with x=0.1-0.5 (short LSF or LSF-X0) catalyst, PO yield is similar or doubled compared to Ag and Pt catalysts, respectively, with strongly improved selectivity. $(La_{1-x}Sr_x)Mn_zO_3$ with x=0.1-0.5 and z>0.9 (short LSM or LSM-X0) catalyst provides significantly higher yield and selectivity; about 1% yield is reached with highest selectivity at lower temperature.

Of course any suitable temperature or ratio of propene (or another alkene) to oxygen can be used to synthesize propylene oxide (or another alkylene oxide). In embodiments, the ratio of propene (or other alkene) to oxygen is about 0.5:1 or greater, such as about 1:1 or greater, or 2:1 or greater. In embodiments, the reaction temperature can be from about 400° C. to about 650° C., such as from about 450° C. to about 550° C. or about 500° C.

While any suitable, or no, voltage can be applied to an electrochemical cell including a catalyst electrode as described herein, in embodiments, voltage between −3V and +3V can be applied. Over long periods of time, a voltage of from about 0.1V to about 1 V, such as from about 0.1V to about 0.7 V can be applied. In embodiments, the voltage can be applied such that the catalyst electrode is the anode.

A number of embodiments of methods for synthesizing alkylene oxides such as propylene oxide are described herein. A summary of selected aspects of such methods is provided below.

In a first aspect, a method for producing propylene oxide includes reacting oxygen and propene in the presence of a metal oxide catalyst, which optionally serves as an electrode of an electrochemical cell, to produce propylene oxide. The ratio of propene to oxygen is about 0.5:1 or greater.

A second aspect is a method of the first aspect, further comprising applying a voltage to the electrochemical cell.

A third aspect is a method of the second aspect, wherein the voltage is applied to the electrochemical cell such that the metal oxide catalyst electrode is anodic.

A fourth aspect is a method of the third aspect, wherein the anodic potential is from about 0.1V to about 0.7V.

A fifth aspect is a method of any one of the preceding aspects, wherein the electrochemical cell comprises an oxygen ion conducting electrolyte.

A sixth aspect is a method of the fifth aspect, wherein the oxygen ion conducting electrolyte comprises doped zirconia.

A seventh aspect is a method of any one of the preceding aspects, wherein the metal oxide catalyst is a noble metal-free catalyst.

An eighth aspect is a method of any one of the preceding aspects, wherein the metal oxide catalyst comprises a transition metal.

A ninth aspect is a method of any one of the preceding aspects, wherein the metal oxide catalyst comprises a perovskite catalyst.

A tenth aspect is a method of the ninth aspect, wherein the perovskite catalyst comprises a Fe or a Mn catalyst.

An eleventh aspect is a method of any one of the preceding aspects, wherein the temperature is from about 400° C. to about 650° C.

A twelfth aspect is a method of any one of the preceding aspects, wherein the temperature is about 500° C.

A thirteenth aspect is a method of any one of the preceding aspects, wherein the ratio of propene to oxygen is about 1:1 or greater.

A fourteenth aspect is a method of any one of the preceding aspects, wherein the ratio of propene to oxygen is about 2:1 or greater.

A fifteenth aspect is a method for producing propylene oxide that includes reacting oxygen and propene in the presence of a metal oxide catalyst free of a noble metal to produce propylene oxide. The ratio of propene to oxygen is about 0.5:1 or greater.

A sixteenth aspect is a method of the fifteenth aspect, wherein the metal oxide catalyst comprises a transition metal.

A seventeenth aspect is a method of the fifteenth aspect or the sixteenth aspect, wherein the metal oxide catalyst comprises a perovskite catalyst.

An eighteenth aspect is a method of the seventeenth aspect, wherein the perovskite catalyst comprises a Fe or a Mn catalyst.

A nineteenth aspect is a method of any one of aspects 15-18, wherein the temperature is from about 400° C. to about 650° C.

A twentieth aspect is a method of any one of aspects 15-19, wherein the ratio of propene to oxygen is about 1:1 or greater.

In the following, non-limiting examples are presented, which describe various embodiments of the methods discussed above.

EXAMPLES

In the following examples, processing of an electrolyte-supported catalyst, test reactor set up and operation, as well as reaction product analysis by gas chromatography are described. Examples of noble metal and perovskite catalyst performance are provided for the direct epoxidation of propylene under open circuit conditions and under cell voltage.

Example 1: Processing of Electrolyte-Supported Oxide Catalysts

A 20 μm thick 3YSZ (3 mol % yttria stabilized zirconia) electrolyte film (U.S. Pat. No. 5,089,455) is employed as oxygen ion conducting electrolyte to support oxide catalysts. The electrolyte sheet is cleaned in diluted HF solution and washed in deionized water prior to use.

$(La_{0.8}Sr_{0.2})Mn_{1.03}O_4$ (LSM), $(La_{0.8}Sr_{0.2})FeO_4$, x=0.2, 0.3, 0.4 (LSF-20, LSF-30, LSF-40) powders with about 100 nm particle size are mixed with a printing vehicle, screen-printed on the 3YSZ electrolyte and fired in air at temperatures between 1100° C. and 1250° C. for 1-4 h. The fired print thickness is 1-3 μm. Electrically conducting contacts are applied to the oxide layer by printing a Pt/YSZ or Ag/YSZ comb-shaped pattern on top of the oxide print and firing it to 1200° C. for Pt and 850-950° C. for Ag, respectively, or by simply connecting electric conducting wire to the border of the catalyst area. A large fraction of the oxide catalyst surface is uncovered. In order to extract the catalyst/substrate activity, comparative catalytic evaluations are run for gas combustion in the same set up with an empty sample holder and also for catalyst-free samples that had only an Ag/YSZ or Pt/YSZ electric full or comb-shaped contact layer.

X-ray diffraction of the oxide layers shows no additional phases besides perovskite. The perovskite lattice parameter varied with Sr-substitution. SEM of oxide surfaces and cross sections do not show any additional phases for an optimized firing in air. Interfaces between YSZ electrolyte and perovskite layer also show no signs of chemical reaction. Additional phase formation is only observed for conditions that are not in the optimum composition-firing temperature-firing environment window. For example, formation of pyrochlore is observed in LSM samples when fired at temperatures above 1200° C. or for Mn-deficient powder. Another example is the appearance of brownmillerite in oxygen-deficient LSF after exposure to heavily reducing conditions.

Figure 3A:
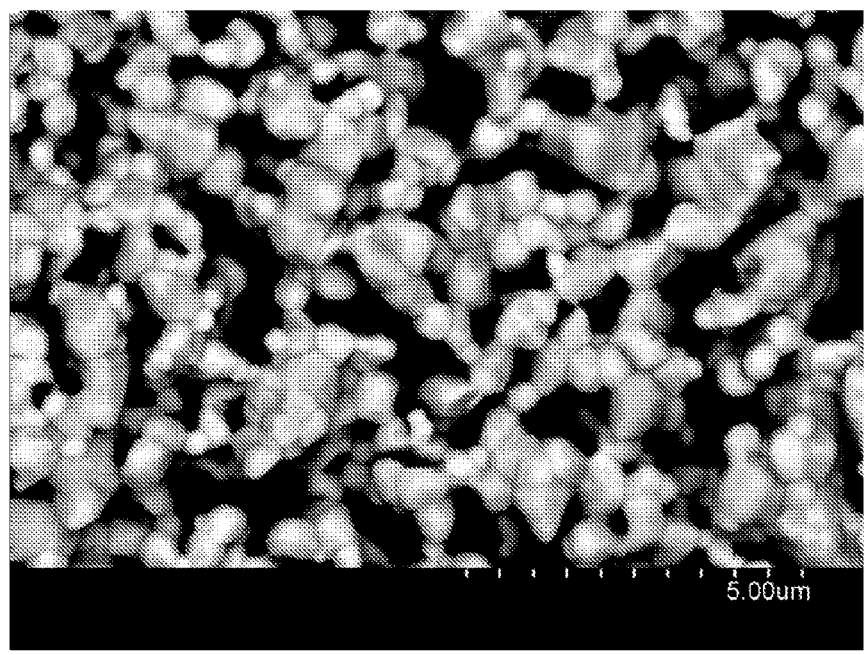
FIGS. 3A-B are scanning electron microscope (SEM) images of an as-processed YSZ-electrolyte supported perovskite catalyst layers: $(La_{0.8}Sr_{0.2})Mn_{1+x}O_3$ (A); $(La_{0.8}Sr_{0.2})FeO_3$ (B).
Figure 3B:
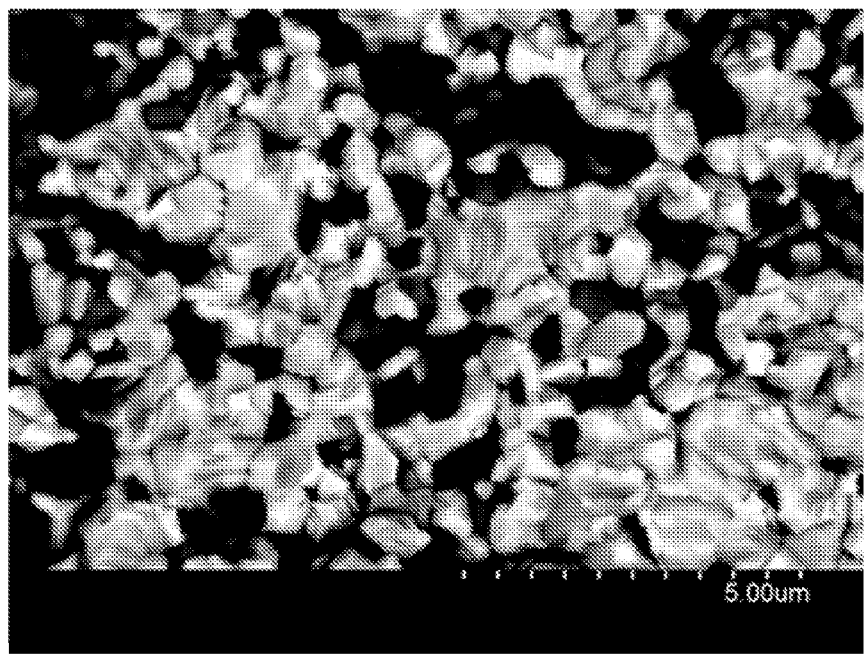

FIG. 3A-B show SEM views of representative YSZ electrolyte-supported mixed oxide catalyst layers of LSM (A) and LSF (B) after processing.

Example 2: Catalyst Stability During Operation

Figure 4A:
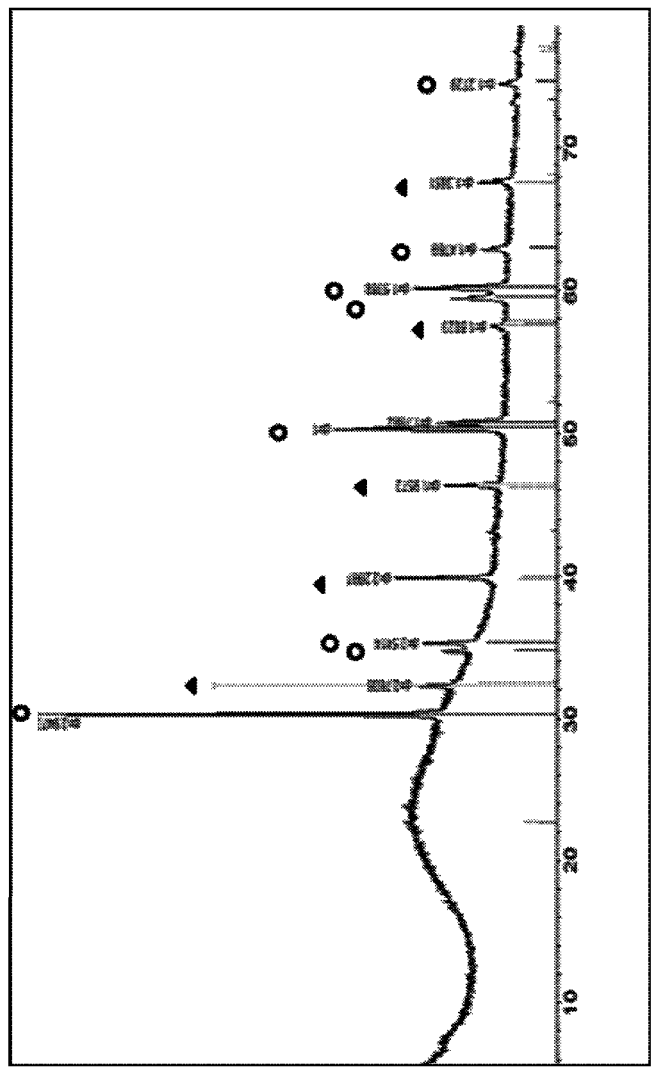
FIGS. 4A-D are images, results and data of phase and microstructure characterization showing no evolution or degradation of the oxide catalyst during operation.
Figure 4B:
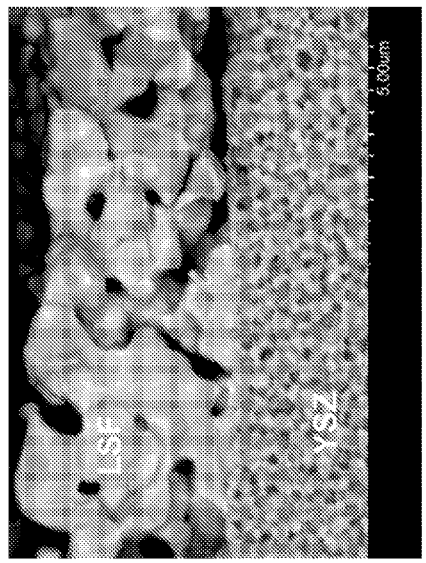
Figure 4C:
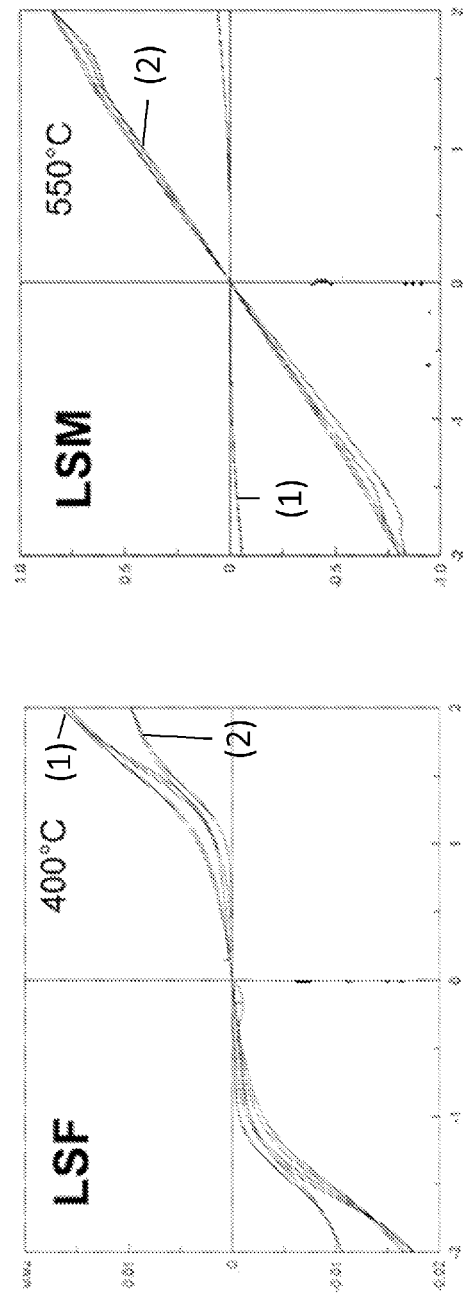
Figure 4D:
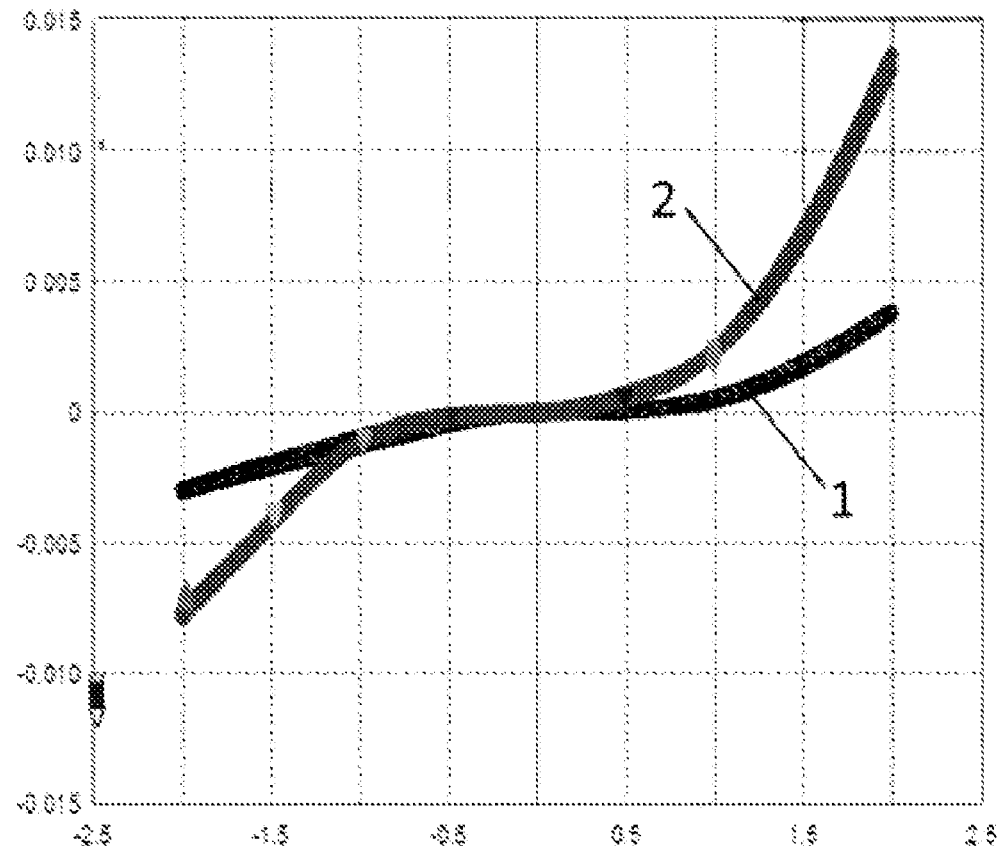

Within normal catalyst operation (e.g., avoiding excessive applied cell voltage of 2.5V or more, excessive temperatures of 700° C. or more and exposure of the catalyst to hydrocarbon without oxygen or to $p_{O2}<10^{-20}$ bar), the oxide catalysts are stable. They are not degraded by exposure to hydrocarbon/oxygen mixtures or by exposure to the reaction side products, water and $CO_2$. FIGS. 4A-D show the phase and microstructure of operated oxide catalyst. FIG. 4A shows XRD of electrolyte-supported perovskite catalyst after processing and after longtime operation in propene/oxygen at 550° C.; only a single perovskite phase is visible in the $(La_{0.8}Sr_{0.2})FeO_3$ catalyst layer (together with peaks from the underlaying zirconia substrate). Circles=$(La_{0.8}, Sr_{0.2})FeO_3$ perovskite; triangles=tetragonal zirconia 3YSZ substrate. FIG. 4B shows SEM of polished cell cross sections of processed and operated cells; no microstructural modification of the catalyst or the catalyst/electrolyte interfaces is noticeable. FIG. 4C shows i-V curves for cells with LSF or LSM oxide catalysts in oxygen [(1) 1% $O_2$ in Ar] and in oxygen/propene [(2) 0.5% $O_2$+0.5% propene in Ar]. It can be seen that the oxygen incorporation rates in propene/oxygen mixtures compared to those in oxygen are similar for LSF and significantly accelerated for LSM, demonstrating that the oxide catalyst surface is not degraded by operation in propene-containing gas mixtures. FIG. 4D shows i-V curves for cells with LSF oxide catalyst in humid (1) and dry (2) oxygen-containing environment. It can be seen that the oxygen incorporation rates in humid oxygen mixtures compared to dry ones for LSF show no current penalty, demonstrating that the oxide catalyst surface is not degraded by operation in humid gas mixtures as for example the case when full combustion side product water forms during hydrocarbon oxidation.

Example 3: Testing Procedure Used for Evaluating Electrolyte-Supported Oxide Catalysts For testing the YSZ-supported oxide catalyst in a small electrochemical reactor, oxide catalyst samples with 1-2 $cm^2$ macroscopic surface area are used. As counter electrode either the same oxide catalyst or a perovskite/YSZ layer with a partially or fully covering conductive Pt/YSZ or Ag/YSZ print is used. The samples were mounted via Ag-net and wire onto an alumina sample holder that was equipped with a thermocouple close to the oxide layer. The oxide catalyst layers are connected to a power source. To allow application of a cell voltage and simultaneous electrochemical measurements, the cells are mounted in a symmetric two-electrode, four-wire set up. A Solartron 1260 Frequency Response Analyzer with 1287 Electrochemical Interface is used to apply the cell potential, measure i-U characteristics and impedance in a range from 0.01 Hz to 300,000 Hz.

The sample holder is introduced into a ceramic reactor tube of 250 ml volume. The reactor was closed gas-tight with a metallic cap and O-ring. Gas is introduced into the ceramic reactor tube via a gas inlet ceramic tube. Reactor outlet gas is captured at the end of a gas outlet tube. The reactor inlet gas flow is in the range of 0.2-1 cfh. Mixtures of propene and air are used as inlet gas with ratios from 10:1 to 1:10 at absolute concentrations from 0-2% and 0-21%, respectively; nitrogen or argon are used as inert carrier gas. Gases are mixed and blended using a gas control unit with electro-valves. A schematic diagram illustrating the experimental set up used is depicted in, and as discussed above with regard to, FIG. 2.

Reaction products are analyzed at the reactor outlet by a gas chromatograph (Agilent MicroGC). The gas chromatograph is equipped with CPsil5, alumina and molecular sieve columns, operated at 50, 110 and 30° C., respectively, and run at optimized settings for gas detection and separation of the various propene oxide homologues. Acrolein, propylene oxide, allylalcohol, isopropanol and acetone can be separated on the CPsil5 column. Propene, $CO_2$ and $H_2O$ can be detected. The GC is run in flow-by mode with He as carrier gas. At least 18 acquisitions are run to clean the columns for every change in reactor setting. The reactor inlet gas is analyzed to determine gas impurities; reference spectra of the reactor under inert gas flow are taken at different reactor temperatures to determine contaminants from the reactor itself.

Figure 5A:
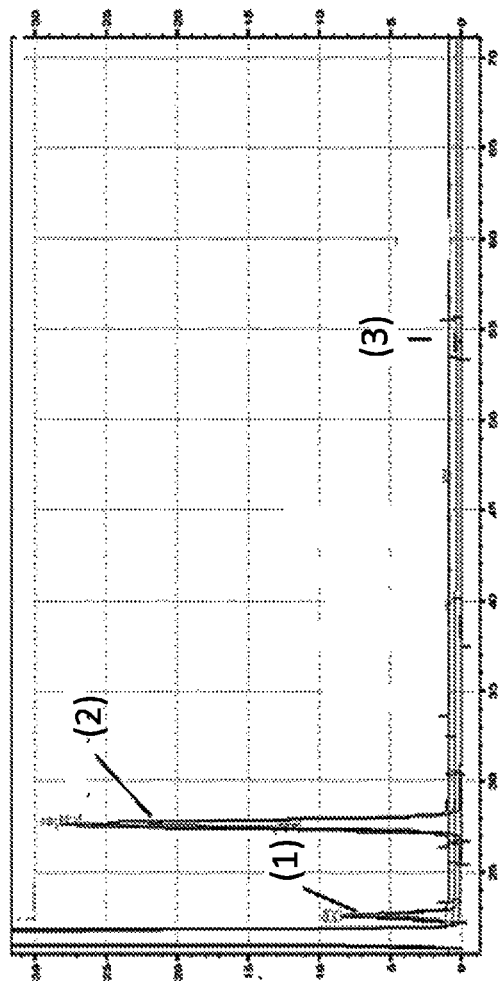
FIG. 5A shows typical gas chromatograms acquired with a CPsil 5 column at 50° C., 22 bar for reactor outlet gas when using propene/oxygen/Ar=2:1:60 at 0.3 cubic feet per hour (cfh) flow rate for a LSM-20 catalyst at different temperatures (700° C., 550° C., 450° C.). Peak retention times were attributed based on calibration and cross-comparison. The CPsil 5 column provides a separation by boiling point.
Figure 5B:
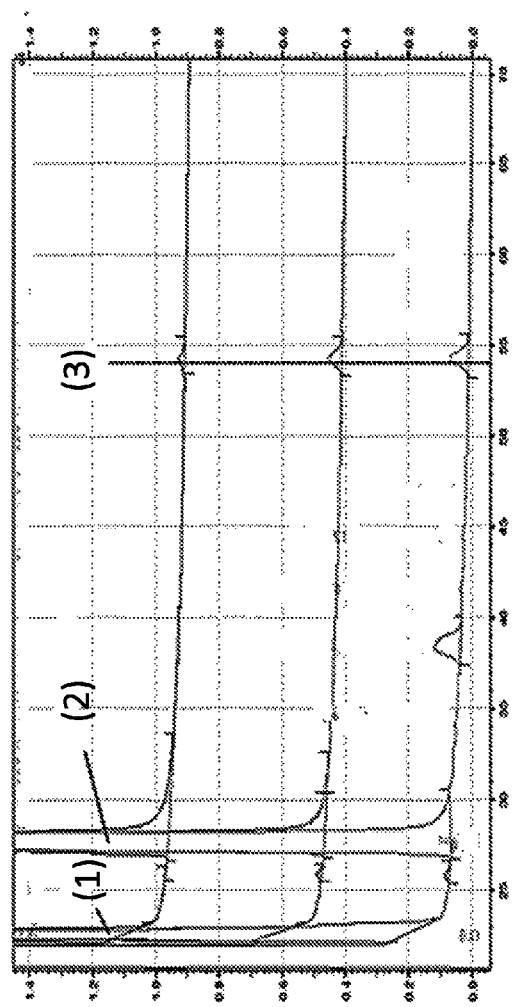
FIG. 5B is an enlargement of a portion of FIG. 5A.
Figure 5C:
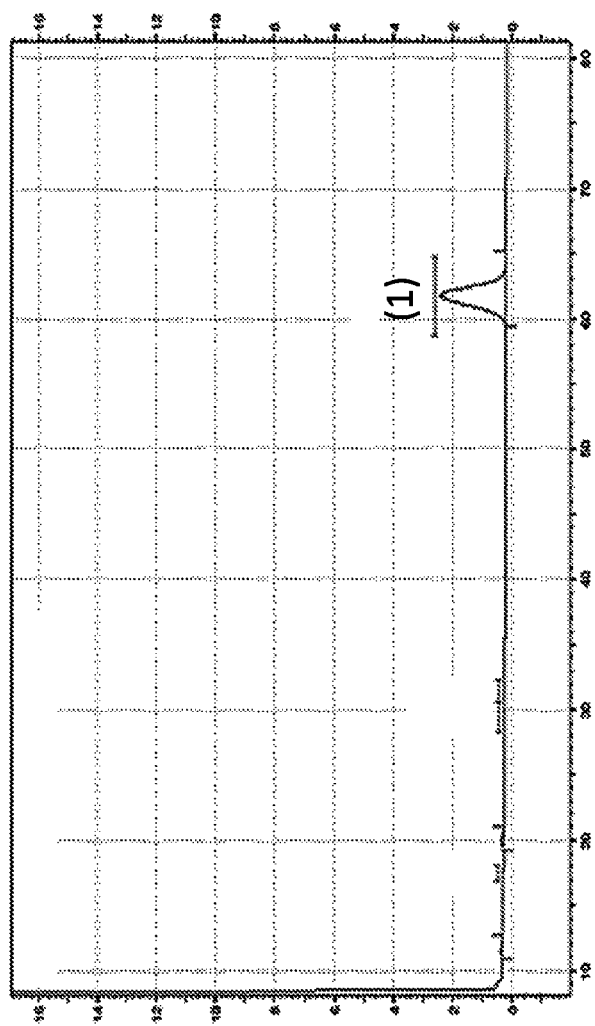
FIG. 5C is a corresponding GC spectra to FIG. 5A acquired with a molsieve column at 30° C., 22 bar.

FIGS. 5A-C shows a typical set of gas chromatograms (CPsil5 column operated at 50° C., 22 psi) for the reactor outlet gas when using propene/oxygen/Ar=2:1:60 at 0.3 cfh flow rate for a LSM-20 catalyst at different temperatures (700° C., 550° C., 450° C.) (FIG. 5A). Peak retention times are attributed based on calibration and cross-comparison. In FIGS. 5A-B, peak (1) corresponds to $CO_2$, peak (2) corresponds to propylene, and peak (3) corresponds to propylene oxide. FIG. 5B is an enlargement of a section of FIG. 5A, highlighting the propylene oxide peak (3). The top trace corresponds to 700° C., the middle trace corresponds to 550° C., and the bottom trace corresponds to 450° C. FIG. 5C is a GC spectra acquired with mol sieve column at 30 C, 22 bar, showing $H_2O$ (1) as another key product.

Figure 6A:
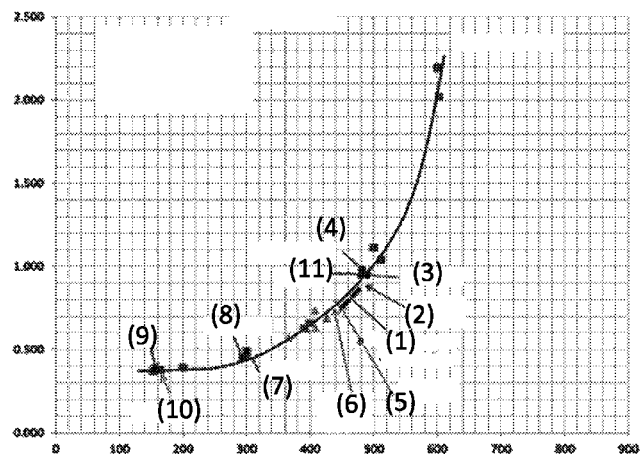
FIGS. 6A-B demonstrate separation of propylene oxide and homologous side products that were achieved using a MicroGC set up with CPsil5 column operated at 50° C., 22 bar. (A) Calibration and (B) separation potential are shown to illustrate identification and semi-quantification of propylene oxide.
Figure 6B:
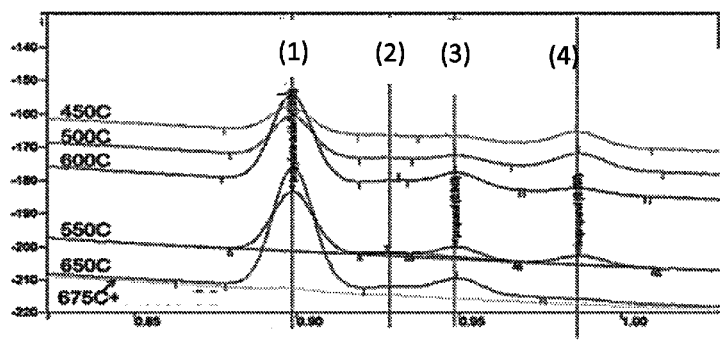

FIGS. 6A-B show the calibration (A) that is used for the CPSil5 column and the separation (B) that is achieved under the above described GC operation conditions. For FIG. 6A, (1)=propylene oxide, expected; (2)=acrolein, expected; (3)=propanal; (4)=isopropanol; (5)=ethanol; (6)=epoxide, expected; (7)=propane; (8)=propene; (9)=$CO_2$; (10)=ethane; (11)=acetone; x-axis=retention time from literature for CPSIL5 or similar columns; and y-axis=retention time in minutes, observed, on CPSIL5 (50° C., 22 bar). For FIG. 6B, (1)=propylene oxide; (2)=acrolein; (3)=propanal; (4)=isopropanol; x-axis is retention time on the used GC; y-axis is microvolts; and the * next to 675° C. indicated excess $O_2$.

Example 4: Comparative Test Results for Uncatalyzed Combustion of Propene-Oxygen Gas Mixtures In order to separate catalytic conversion from the naturally occurring high temperature combustion, the high temperature gas combustion is evaluated. Simple uncatalyzed gas combustion is mimicked in the test reactor by operation in oxygen-propene gas mixtures without any catalyst in presence. The reactor reaction products are identified and quantified for different propene/oxygen gas mixtures in the temperature range from room temperature to 750° C.

Figure 7A:
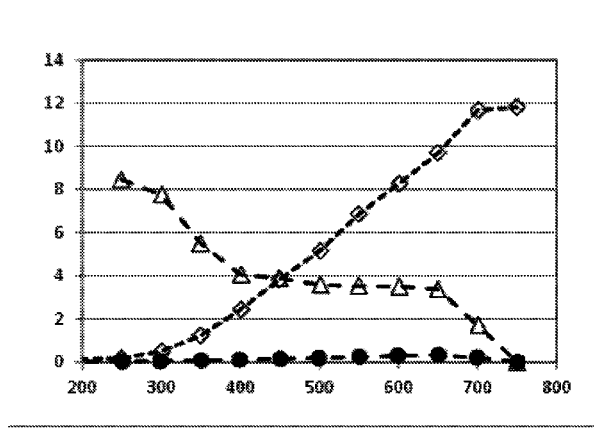
FIGS. 7A-B illustrates yield and selectivity of propylene oxide for gas combustion.
Figure 7B:
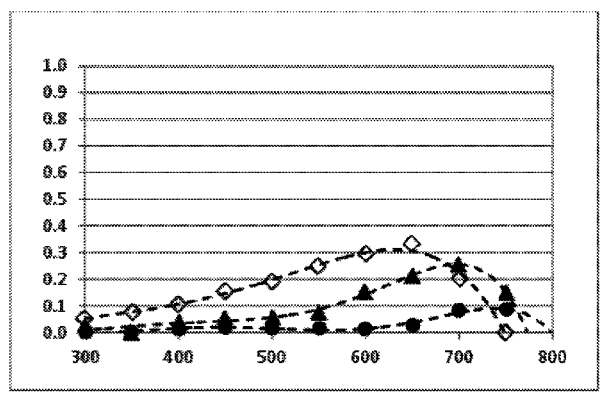

The reaction is found to initiate at around 300° C. Under the reactor operation conditions within the test reactor design, the main reaction products are $CO_2$ and $H_2O$. Propylene oxide is one of the other products. FIGS. 7A-B illustrate propylene oxide yield and selectivity for the uncatalyzed gas combustion. Isopropanol is an important side product at temperatures below 600° C., while, at temperature above 600° C., increasing fractions of butadiene, butene, ethylacetate and lighter oxidized fragments formed (increasing levels with increasing propene/oxygen ratios). At high temperatures, 700° C. and more, almost all oxygen was consumed under $CO_2$ formation (The total equivalent of all oxygen is 12% carbon dioxide). FIG. 7A shows results for gas combustion of 1% $O_2$ and 1.8% propene in argon as function of temperature. It includes the unconverted fraction of propene, propylene oxide yield and the selectivity for propylene oxide. For FIG. 7A, open diamonds=⅓ $CO_2$ yield; filled circles=PO yield; open triangles=PO selectivity; x-axis=temperature (° C.); and y-axis is % yield of PO, $CO_2$, PO selectivity. FIG. 7B presents the yield of propylene oxide as function of temperature for gas combustion of different propene-oxygen gas mixtures. For FIG. 7B, open diamonds=1 propene: 0.5 $O_2$; filled triangles=1 propene: 1 $O_2$; filled circles=1 propene: 2 $O_2$; x-axis=temperature (° C.); and y-axis id epoxide yield in %. The natural propylene oxide yield does not exceed about 0.3% and reaches maximum yield only at temperatures above 600° C. Maximum yield was found around the propene:oxygen=2:1 ratio. Yield decreases with increasing oxygen content and the maximum yield is shifted to higher temperature.

Example 5: Propylene Oxidation on Pt/YSZ Catalyst

The examination of Pt/YSZ layers on YSZ electrolyte serves for two purposes: 1) evaluation of a noble metal catalyst, 2) the evaluation of the Pt/YSZ catalyst provides an estimate of the Pt/YSZ electric contact layer catalytic contribution to the total catalytic conversion provided in cells with oxide catalyst and electric contact.

Propene-oxygen mixtures are reacted in a 250 $cm^3$ size test reactor with a Pt-based catalyst sheet of 1-2 $cm^2$ surface area. The catalyst is a Pt/YSZ porous composite layer. Reaction products are identified and quantified for the heterogeneously catalyzed reaction with different propene/oxygen gas mixtures in the temperature range from room temperature to 750° C. The reaction initiated around 300° C. Under the reactor operation conditions (determined by the test reactor design and gas flow), $CO_2$ and $H_2O$ are the main reaction products. Propylene oxide is under the additional products. Maximum PO yield is up to 0.4% for a wide range of gas mixtures and temperatures. The selectivity for PO ranges between 0.002 and 0.015. It increases monotonously with increasing temperature and increasing oxygen/propene ratio. Besides PO, other hydrocarbons are formed: butadiene, butene, ethylacetate, isopropanol. For high hydrocarbon/oxygen ratios, the platinum catalyst is poisoned at low temperature; CO poisoning of platinum is a well-known problem.

Figure 8A:
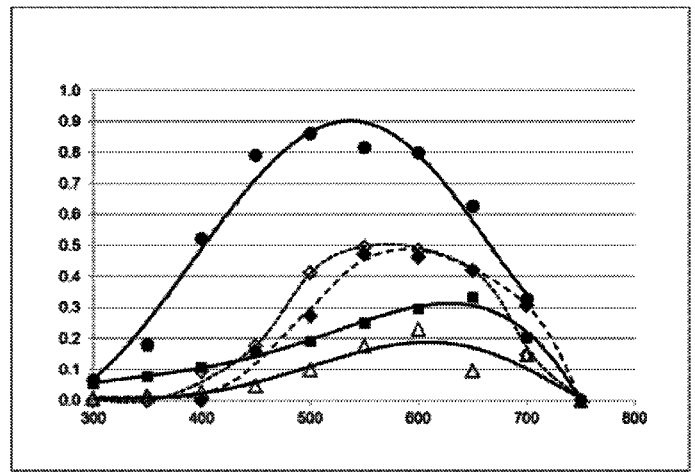
FIGS. 8A-C show a comparison of uncatalyzed and catalyzed propylene oxidation for a selected propene/oxygen gas mixture (ratio 2:1 in Ar) on Pt/YSZ, Ag(Pd)/YSZ, LSM-20, LSF-40 catalyst; for comparison, data for the uncatalyzed gas combustion are added. (Results were obtained for 1 $cm^2$ catalyst sheet in a 250 ml reactor with 0.3 cfh gas flow of Ar-diluted gas.) (A) Propylene oxide yield. The comparative data show that Pt catalyst poisoning produces lower yield than uncatalyzed gas combustion. Yield increase can be noticed for metallic silver-based catalyst and also for LSF-40 and LSM. Large increase in yield is observed with LSM-20 catalyst; the best temperature range is 500-600° C. (B) $CO_2$ production. While uncatalyzed gas combustion shows a linear increase in $CO_2$ yield with temperature until approaching the oxygen-limited threshold, the heterogeneously catalyzed reactions all show very similar curve shape with a rapid increase at low temperature above the simple gas combustion yield that is followed by a plateau and, at high temperature, exponentially increases and approaches the gas combustion threshold. (C) The selectivity for propylene oxide is bad on Pt catalyst. Selectivity is similar for Ag and LSF-40 catalysts. It is significantly improved for LSM-20 and constant over a very wide temperature range until it starts to decrease above 600° C. due to contribution of the gas combustion.
Figure 8B:
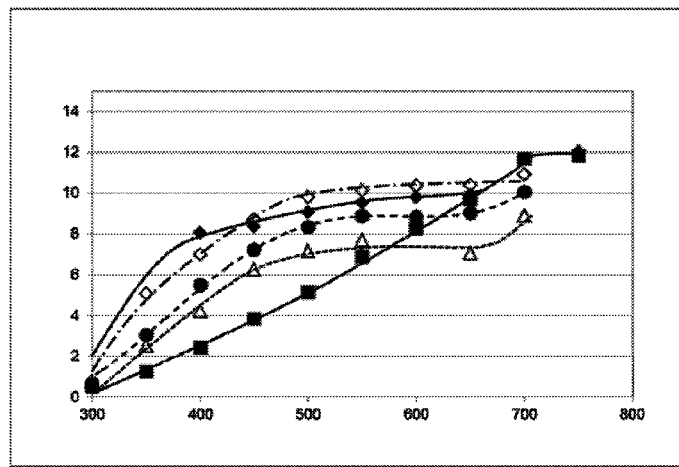
Figure 8C:
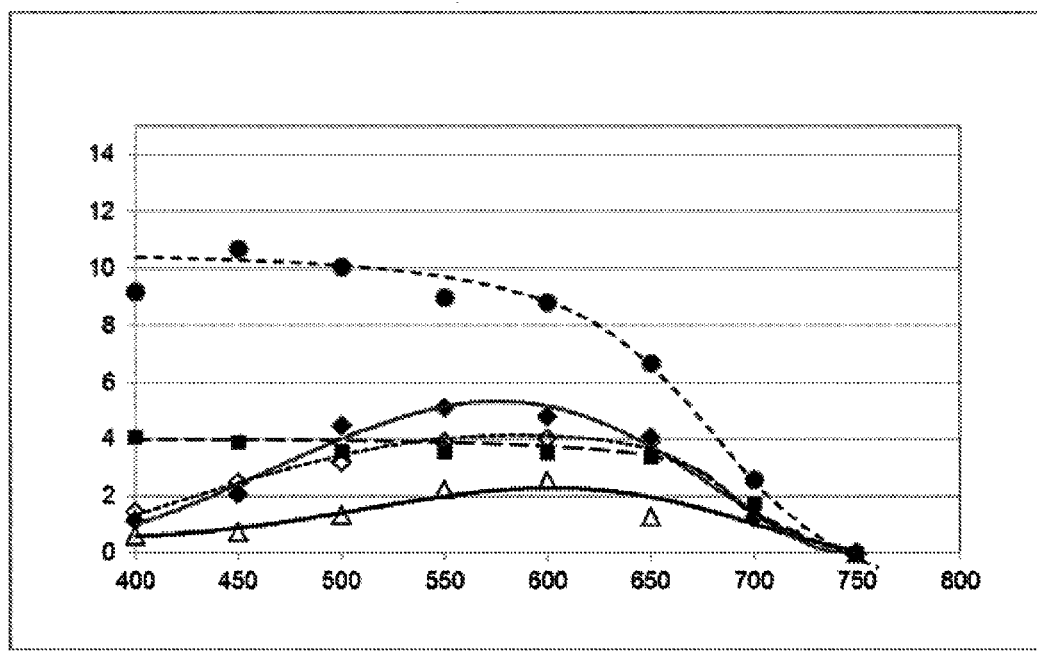

FIG. 8A-C illustrate yield of $CO_2$, PO yield and PO selectivity in the same set up for gas combustion and in presence of a 1 $cm^2$ electrolyte (and adhesion layer)-supported Pt-YSZ catalyst sheet. For FIG. 8A, squares=gas combustion; filled diamonds=LSF-40 catalyst; triangles=Pt catalyst; circles=LSM-20 catalyst; un-filled diamonds=Ag catalyst; x-axis=temperature (° C.); and y-axis id % yield propylene oxide. For FIG. 8B, the shapes are the same as for FIG. 8A; x-axis=temperature (° C.); and y-axis=% yield carbon dioxide. For FIG. 8C, the shapes are the same as for FIGS. 8A and B; x-axis=temperature (° C.); and y-axis=% selectivity propylene oxide. It can be seen that the $CO_2$ yield follows an S-shaped curve compared to the gas combustion curve with improved carbon dioxide yield at lower temperatures. Largest improvement is visible at around 450° C. At temperatures around 700° C., the Pt-catalyzed yield curve approaches the combustion yield. While $CO_2$ and $H_2O$ yield are increased by the Pt-catalyst, the propylene oxide yield obtained for a propene:oxygen=2:1 mixture is smaller for all reaction temperatures, FIG. 8B. For higher propene levels, further decrease in propylene oxide yield compared to the gas combustion yield is observed, that clearly indicates a poisoning of the Pt catalyst in gas mixtures with high propene content. The low PO yield for this type of cell indicates that a Pt/YSZ-based electric contact does not provide additional catalytic conversion beyond the gas combustion.

Example 6: Propylene Oxidation on Tuned Pt/YSZ Catalyst

Figure 9A:
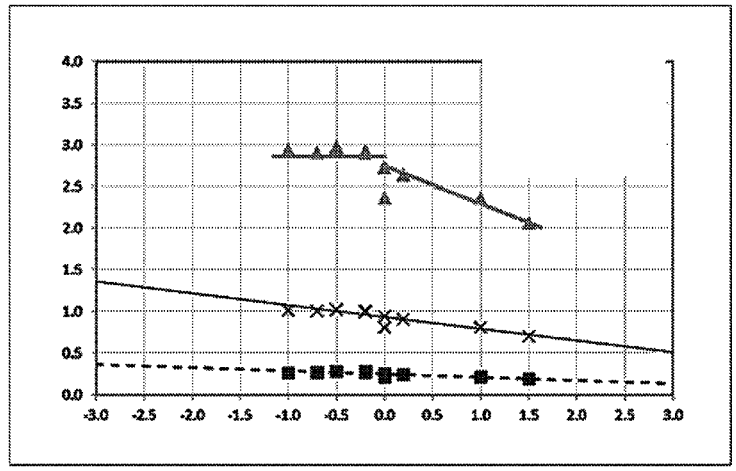
FIG. 9A is a graph showing the effect of cell voltage for Pt-based catalyst on $CO_2$ yield, PO yield and PO selectivity.
Figure 9B:
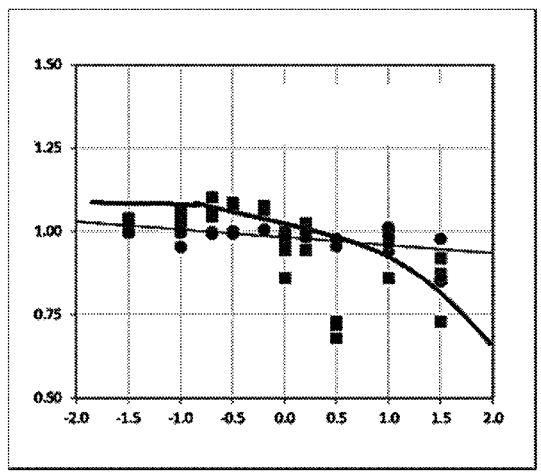
FIG. 9B is a graph showing relative change in $CO_2$ and PO yield with applied cell voltage at 550° C. in propene:oxygen gas mixture 2:1 in Argon.

Application of a cell voltage influences the reaction yield and products formed with the platinum-based catalyst. FIGS. 9A-B illustrate $CO_2$ and PO yield and PO selectivity in the same set up as in Example 5 for a 1 $cm^2$ electrolyte (and adhesion layer)-supported Pt-YSZ catalyst sheet under cell voltage. For FIG. 9A, triangles=selectivity PO; X's=PO/$CO_2$; squares=yield propoxide; x-axis=applied potential (V); and y-axis=% yield, selectivity or ratio. For FIG. 9B, squares=PO at bias/PO at 0V; circles=carbon dioxide at bias/carbon dioxide at 0V; x-axis=applied potential (V); and y-axis=ratio of $CO_2$ or PO at bias/at 0V. The $CO_2$-production is not much affected by the cell voltage and its variation remains negligible. The PO production underwent larger changes; the PO yield remains almost constant or slightly increased under negative cell voltage, while it drops continuously with increasing positive cell voltage. This likely reflects a poisoning of Pt-catalyst under positive cell voltage, corresponding to catalyst poisoning under oxidizing conditions.

Application of a negative potential can be used to reactivate a Pt-based catalyst for direct oxidation of propene. For short exposure times to positive cell voltage, inversing the applied cell voltage remedies the catalyst. For long time exposure of the platinum catalyst to positive electric potential, the catalyst layer irreversibly degrades.

Example 7: Propylene Oxidation on Ag-Based Catalyst

A silver-based catalyst made of YSZ electrolyte-supported Ag(Pd)/YSZ porous composite layer (1 $cm^2$ macroscopic surface area) is tested in the reactor. Reaction products are identified and quantified for the heterogeneously catalyzed reaction in different propene/oxygen gas mixtures in the temperature range from room temperature to 750° C. It is found that the reaction initiated around 350-400° C. Under the reactor operation conditions (within the test reactor design), $CO_2$ and $H_2O$ are the main reaction products. In addition, propylene oxide, butadiene, butene, ethylacetate, isopropanol and acetone are formed. At temperatures of 650° C. and above, a variety of other additional products form with rapidly increasing concentrations with increasing temperature. The PO production is found to decrease for temperatures above 600° C. and vanish at 750° C. The maximum PO yield, 0.5%, is found for a wide range of gas mixtures in the temperature range of 500-600° C. The selectivity for PO varied with temperature and went through a maximum about 0.04 at 550° C. FIG. 8 shows comparative behavior of the Ag(Pd)/YSZ noble metal catalyst in propene/oxygen=2:1 gas mixture as function of temperature. FIG. 9A shows the propylene oxide yield as function of temperature. The silver-based catalyst produces enhanced PO yield compared to the gas combustion. A similar curve shape with increasing yield to a maximum and then decrease to zero with increasing temperature is obtained. PO production onset is above 400° C. Maximum PO yield under these conditions is about 0.5% in the temperature range of 550-600° C. The PO yield of the silver-based catalyst is higher than that produced by gas combustion or Pt-catalyst. FIG. 8B shows comparative results on carbon dioxide yield for the same reaction conditions. The silver-based catalyst also promotes the full combustion and produces a steeper S-shaped $CO_2$ yield with early and steep onset. FIG. 8C presents comparative PO selectivity, illustrating selectivity of around 4% in the temperature range from 500-650° C.

Example 8: Propylene Oxidation on Tuned Ag-Based Catalyst

Figure 10A:
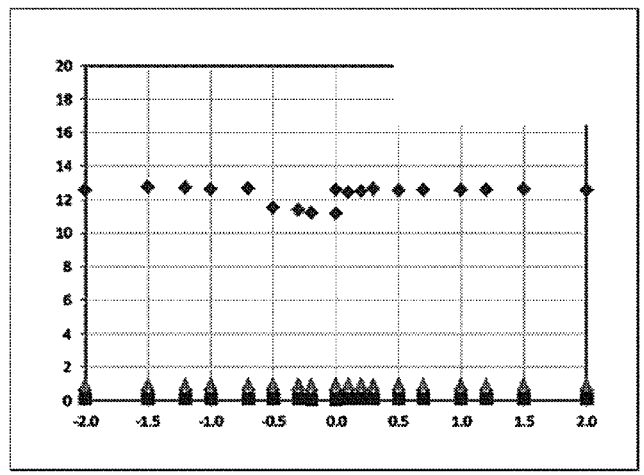
FIG. 10A is a graph showing the effect of cell voltage for Ag-based catalyst on $CO_2$ yield, PO yield and PO selectivity.
Figure 10B:
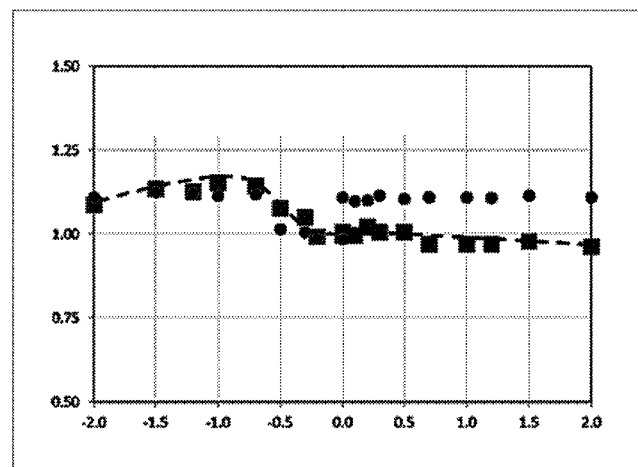
FIG. 10B is a graph showing relative change in $CO_2$ and PO yield with applied cell voltage at 550° C. in propene:oxygen gas mixture 2:1 in Argon.

FIG. 10A illustrates the effect of cell voltage on $CO_2$ yield, PO yield and selectivity for the Ag-based catalyst of Example 7. FIG. 10B shows the relative change in $CO_2$ and PO yield with the applied cell voltage at 550° C. in propene:oxygen gas mixture 2:1 in Argon in an asymmetric cell. For FIG. 10A, diamonds=reaction yield; squares=yield propoxide; triangles=selectivity PO; x-axis=applied potential (V); and y-axis=% yield, selectivity or ratio. For FIG. 10B, squares=PO at bias/PO at 0V; circles=$CO_2$ at bias/$CO_2$ at 0V; x-axis=applied potential (V); and y-axis=ratio of $CO_2$ or PO at bias/at 0V. Applied cell voltage resulted in increase of only full combustion, visible in the $CO_2$-production, or full combustion and PO production. Under applied positive cell potential, $CO_2$ production is increased, while the PO yield remains unaffected. Negative cell potential produces yield increase for both, $CO_2$ and PO. A relative PO yield increase of about 10% is demonstrated at 550° C. for an applied cell voltage in the range of −0.7V to −1V.

Example 9: Propylene Oxidation on Fe-Perovskite

The comparative presentations of PO yield, carbon dioxide yield and PO selectivity in FIG. 8 includes data for LSF-40 catalyst in a propene-oxygen=2:1 mixture as function of temperature. The LSF-40 catalyst shows similar PO and complete combustion ($CO_2$) yield as the silver-based catalyst with a slightly higher full combustion yield. Maximum PO yield is 0.5% at about 550° C. FIG. 8C illustrates the advantage of a higher low temperature PO selectivity of the oxide catalyst compared to the noble metal silver- and platinum-based catalysts. This advantage is preserved up to temperatures of 500° C.

Figure 11A:
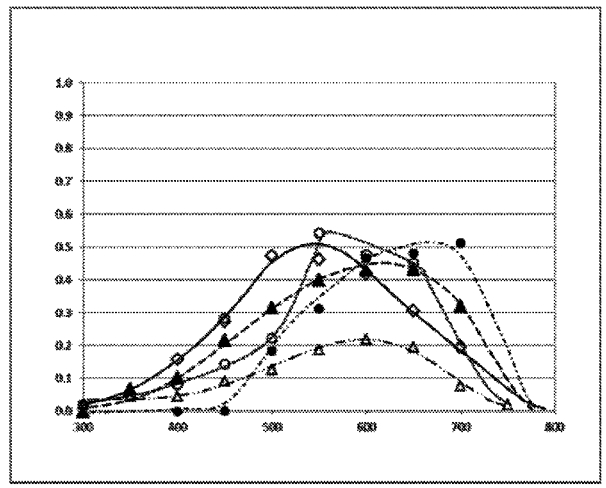
FIGS. 11A-B are graphs showing a comparison of propylene oxide (A) yield and (B) selectivity for LSF-40 catalyzed oxidation of different propene/oxygen gas mixtures in Ar (Results were obtained for 1 $cm^2$ catalyst sheet in a 250 ml reactor with 0.3 cfh gas flow of Ar-diluted gas.). Best yield is achieved at the stoichiometric gas ratio of 1 mole propene: ½ mole $O_2$; selectivity spikes for high propene content in the gas.
Figure 11B:
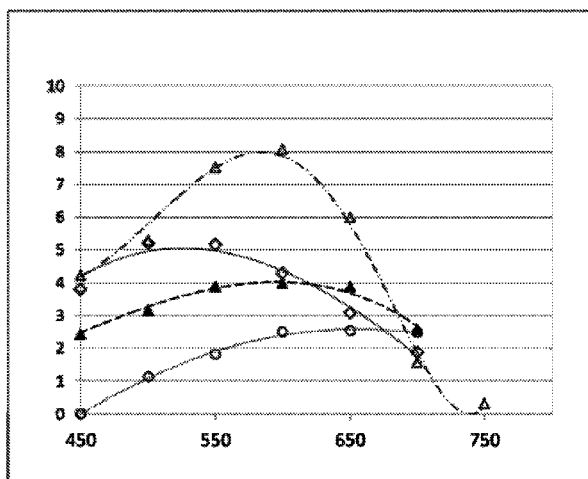

FIGS. 11A-B show a comparison of propylene oxide yield (A) and selectivity (B) for LSF-40 catalyzed oxidation of different propene/oxygen gas mixtures in Ar. For FIG. 11A, open diamonds=2 propene: 1 $O_2$ on LSF-40; open triangles=8 propene: 1 $O_2$ on LSF-40; open circles=1 propene: 1 $O_2$; filled circles=1 propene: 1 $O_2$ on LSF-40; (first cycle of voltage exposure for the cell) filled triangles=2 propene: 1 $O_2$ on LSF-40 (later cycle of exposing the cell); x-axis=temperature (° C.); and y-axis=% yield, selectivity. For FIG. 11B, open diamonds=2 propene: 1 $O_2$ on LSF-40; open triangles=8 propene: 1 $O_2$ on LSF-40; open circles=1 propene: 1 $O_2$ on LSF-40; closed triangles=2 propene: 1 $O_2$ on LSF-40; x-axis=temperature (° C.); and y-axis=% PO selectivity. Results are obtained for a 1 $cm^2$ size catalyst sheet in a 250 ml reactor with 0.3 cfh gas flow of Ar-diluted gas. Best yield is observed for the stoichiometric gas ratio with 1 molecule propene: ½ molecule $O_2$. Yield of 0.5% PO is reached within a wide range of temperature, while selectivity spikes up to 0.08 for high propene content in the gas. Other hydrocarbon products, such as butadiene, ethyl-actetate, butene form as side products. No acrolein or alcohol formation is observed.

In an overall comparison, Fe-perovskite catalyst provides similar results as Ag-catalyst, but with a higher selectivity for PO and with a lower cost oxide catalyst.

Example 10: Propylene Oxidation on Tuned Fe-Perovskite

Figure 12A:
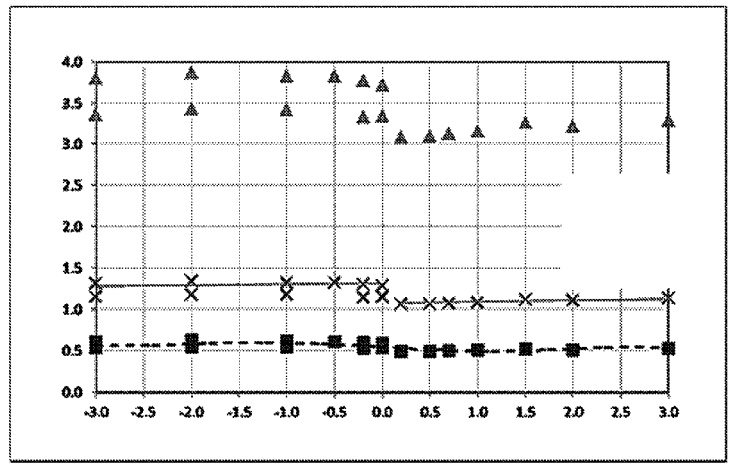
FIG. 12A is a graph showing the effect of electrochemical cell voltage for LSF-based catalyst on $CO_2$ yield, PO yield and PO selectivity.
Figures 12B, 12C:
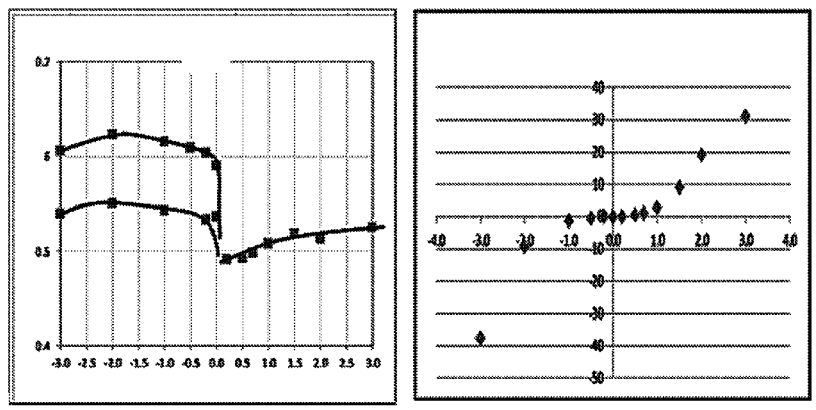
FIG. 12B is a graph showing relative increase in PO yield with cell voltage.
FIG. 12C is a graph showing cell current as function of applied cell potential.

The effect of cell voltage on $CO_2$ yield, PO yield and selectivity for the Fe-perovskite catalyst is illustrated in FIGS. 12A-B. For FIGS. 12A-C, triangles=selectivity PO; squares=yield propoxide; and diamonds=reaction yield. For FIG. 12A, x-axis=applied potential (V); and y-axis=% yield, selectivity or ratio. For FIG. 12B, x-axis=applied potential (V); and y-axis=% yield, PO. FIG. 12A shows the relative change in $CO_2$ and PO yield with applied cell voltage at 500° C. in a propene:oxygen gas mixture 1:1 in Argon. An improvement of the catalyst with applied cell voltage was observed (see, FIG. 12B). For any applied cell potential, $CO_2$ and PO yields are slightly increased. The improvement is larger under negative applied potential. Under negative cell voltage, the PO yield is increased from 0.5 to 0.55 in the initial run and to 0.6% in subsequent runs of cell voltage application. Yield monotonously increased with negative cell potential up to −2V. At more negative cell potential, the yield starts to decrease, most likely due to some permanent degradation of the catalyst under those conditions that could only partially be recovered under zero and positive cell voltage. The maximum overall increase in yield by cell voltage is 20%. FIG. 12C shows i-V characteristics of the cell under applied cell voltage (current in mA/bias in V).

Example 11: Propylene Oxidation on Mn-Perovskite

Reaction products are identified and quantified for the heterogeneously catalyzed reaction of different propene/oxygen gas mixtures on an LSM catalyst (surface 1 $cm^2$) in the temperature range from room temperature to 750° C. The reaction initiates around 300° C. $CO_2$ and $H_2O$ are the main reaction products under the reactor operation conditions and within the test reactor design. Propylene oxide is also formed. The production of side products, such as butadiene, butene and ethyl acetate remain low below 700° C., so that the resulting selectivity of PO was higher than for other catalysts.

FIGS. 8A-C illustrate PO yield (A), yield of $CO_2$ (B) and PO selectivity (C) for the various catalysts described herein. As shown in FIG. 8C, the LSM catalyst shows 10 times better selectivity at low temperature than the other catalysts and still 2× better selectivity at high temperature.

Using the LSM catalyst, a maximum PO yield of 0.9% was reached at zero potential at temperatures between 450° C. to 600° C. This is 2× improvement compared to other oxide and Ag-based catalysts. The large advantage in selectivity was due to the fact that improvement in PO yield was accompanied by a decrease in $CO_2$ production. At temperatures above 650° C., the PO production started to decrease and vanishes around 750° C. A maximum PO yield of 0.9% was reached in the temperature range of 500-550° C.

Example 12: Propylene Oxidation on Tuned Mn-Perovskite

Figures 13A, 13B, 13C:
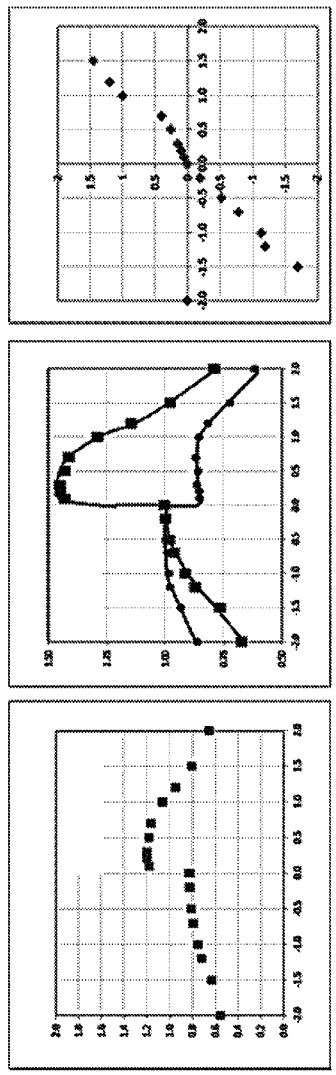
FIGS. 13A-C are graphs showing the effect of electrochemical cell voltage for LSM-catalyst on (A) PO yield, (B) relative $CO_2$ yield, PO yield and on cell current (C). A substantial increase in PO yield is observed for positive cell voltage in a voltage window from +0.1V to +0.7V, where the relative yield is improved by about 50%, while the $CO_2$ production decreases. At higher positive cell voltage, the improvement decays due to catalyst degradation under very high potential. Under negative cell potential, a monotonous decrease of the catalyst performance is observed with a simultaneous decrease in PO and $CO_2$ yield.

FIGS. 13A-C illustrates for LSM-based catalyst (1 $cm^2$) the beneficial effect of cell voltage on PO yield and selectivity (A). In FIG. 13A, squares=yield propoxide; x-axis=applied potential (V); and y-axis=% yield propoxide. The relative change in $CO_2$ and PO yield by applied cell voltage are shown for 500° C. in propene:oxygen gas mixture 2:1 in Argon (FIG. 13B). In FIG. 13B, squares=PO at bias/PO at 0V; circles=$CO_2$ at bias/$CO_2$ at 0V; x-axis=applied potential (V); and y-axis=ratio of $CO_2$ or PO under cell voltage U/$CO_2$ or PO in cell without any applied cell voltage (U=0V). FIG. 13C shows i-V characteristic of the cell under applied voltage (current in mA/bias in V). A substantial increase in PO yield is observed for positive cell voltage in a voltage window from +0.1V to +0.7V, where the relative yield is improved by about 50%, while the $CO_2$ production was decreased. Maximum yield is 1.5% PO. At higher positive cell voltage, the improvement starts to decay due to degradation of the catalyst under undesirable condition. Under negative cell potential, a monotonous decrease of the catalyst performance is observed with a simultaneous decrease in PO and $CO_2$ yield.

In conclusion, a substantial increase in PO yield and selectivity is observed under same experimental conditions for (La,Sr)$MnO_3$ mixed oxide catalyst. The yield with this lower cost catalyst is doubled compared to that of a silver catalyst and shows much higher selectivity, about ×10 at low temperature and ×2 at high temperature. Electrochemical catalyst operation allows tuning the catalyst to even better performance. Under cell voltage, the catalyst performance can be further tuned so that 1.5% propylene oxide yield is reached for 1 $cm^2$ catalyst surface in a 25 $cm^3$ reactor volume.

Even though the relative yield improvement is large, absolute yields in the test reactor are small, because of a small size catalyst sheet (1 $cm^2$) in a large reactor volume (250 $cm^3$), a low flow rate (0.3 cfh) and an unfavorable reactor geometry (gas flow parallel to catalyst sheet). 1.5% epoxide yield in test configuration promises yields of interest at an industrial scale under operation at higher reactive gas pressure, high gas flow rates and with larger catalyst surface area.

Comparison of Different Catalysts

Table 1 summarizes propylene oxide yield and selectivity for LSM and LSF oxide catalysts, Ag and Pt noble metal catalysts, without any applied cell voltage and under (best) cell voltage; gas combustion (no catalyst) data are added. Temperatures are indicated. The gas mixture used for the data of this table contain a ratio of propene and oxygen 2:1. The table provides also comparative ratios of relative yield increase compared to yield obtained with Pt-catalyst and relative yield increase through cell voltage. Results are obtained for 1 $cm^2$ catalyst sheet in a 250 ml reactor with 0.3 cfh gas flow of Ar-diluted gas.

TABLE 1

Propylene oxide yield and selectivity using various catalysts and conditions

| Catalyst | PO yield (no U) | Selectivity (no U) | Temp. (° C.) | PO yield under U | Po yield/PO yield (Pt) | PO yield (U)/PO yield (no U) |
|---|---|---|---|---|---|---|
| LSM | 0.95% | 10% | 500 | 1.5% | 5 | 1.6 |
| LSF | 0.5% | 4.3% | 550 | 0.8% | 2.5 | 1.6 |
| Pt | 0.2% | 2% | 600 | <0.2% | 1 | $<1_{(-3V, +3V)}$ |
| Ag | 0.5% | 5% | 550 | 0.6% | 2.5 | 1.2 |
| None | 0.3% | 3% | >650 | — | 1.5 | |

Thus, embodiments of ALKYLENE OXIDE SYNTHESIS are disclosed. One skilled in the art will appreciate that the reactors and methods described herein can be practiced with embodiments other than those disclosed. The disclosed embodiments are presented for purposes of illustration and not limitation.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to an article, method, system or the like, means that the components of the article, method, system or the like are limited to the enumerated components and any other components that do not materially affect the basic and novel characteristic(s) of the article, method, system or the like.

Also herein, all numbers are assumed to be modified by the term "about" and preferably by the term "exactly." Notwithstanding that the numerical ranges and parameters setting forth the broad scope of the invention are approximations, the numerical values set forth in the specific examples are reported as precisely as possible. All numerical values, however, inherently contain certain errors necessarily resulting from the standard deviation found in their respective testing measurements.

Also herein, the recitations of numerical ranges by endpoints include all numbers subsumed within that range (e.g., 1 to 5 includes 1, 1.5, 2, 2.75, 3, 3.80, 4, 5, etc.). Where a range of values is "up to" a particular value, that value is included within the range.

The words "preferred" and "preferably" refer to embodiments of the invention that can afford certain benefits, under certain circumstances. However, other embodiments can also be preferred, under the same or other circumstances. Furthermore, the recitation of one or more preferred embodiments does not imply that other embodiments are not useful, and is not intended to exclude other embodiments from the scope of the invention.

What is claimed is:

1. A method for producing propylene oxide, comprising:
reacting oxygen and propene in the presence of a mixed metal oxide catalyst to produce propylene oxide,
wherein the mixed metal oxide catalyst serves as an electrode of an electrochemical cell,
wherein the mixed metal oxide catalyst comprises a perovskite catalyst,
wherein the ratio of propene to oxygen is about 0.5:1 or greater,
applying a voltage to the electrochemical cell, and
wherein the voltage is applied to the electrochemical cell such that the mixed metal oxide catalyst electrode is anodic.

2. The method of claim 1, wherein an anodic potential is from about 0.1V to about 0.7V.

3. The method of claim 1, wherein the electrochemical cell comprises an oxygen ion conducting electrolyte.

4. The method of claim 1, wherein the oxygen ion conducting electrolyte comprises doped zirconia.

5. The method of claim 1, wherein the mixed metal oxide catalyst is a noble metal-free catalyst.

6. The method of claim 1, wherein the mixed metal oxide catalyst comprises a transition metal.

7. The method of claim 1, wherein the perovskite catalyst comprises a Fe or a Mn catalyst.

8. The method of claim 1, wherein the temperature is from about 400° C. to about 650° C.

9. The method of claim 1, wherein the temperature is about 500° C.

10. The method of claim 1, wherein the ratio of propene to oxygen is about 1:1 or greater.

11. The method of claim 1, wherein the ratio of propene to oxygen is about 2:1 or greater.

12. A method for producing propylene oxide, comprising:
reacting oxygen and propene in the presence of a mixed metal oxide catalyst free of a noble metal to produce propylene oxide,
  wherein the mixed metal oxide catalyst serves as an electrode of an electrochemical cell,
  wherein the metal oxide catalyst comprises a perovskite catalyst,
  wherein the ratio of propene to oxygen is about 0.5:1 or greater,
tuning the electrochemical cell by injecting charge carriers and oxygen into the catalyst.

13. The method of claim 12, wherein the metal oxide catalyst comprises a transition metal.

14. The method of claim 12, wherein the perovskite catalyst comprises a Fe or a Mn catalyst.

15. The method of claim 12, wherein the temperature is from about 400° C. to about 650° C.

16. The method of claim 12, wherein the ratio of propene to oxygen is about 1:1 or greater.

17. The method of claim 1, wherein the ratio of propene to oxygen is from about 1:1 to about 50:1.

* * * * *